(12) United States Patent
Morschhäuser et al.

(10) Patent No.: US 11,208,372 B2
(45) Date of Patent: Dec. 28, 2021

(54) HYDROXY CARBOXYLIC ACID ESTERS, MANUFACTURING PROCESS THEREOF AND USE THEREOF

(71) Applicant: WeylChem Performance Products GmbH, Wiesbaden (DE)

(72) Inventors: Roman Morschhäuser, Mainz (DE); Said Kchirid, Heigenbrücken (DE); Judith Preuschen, Sörgenloch (DE); Bo Kuhse, Wiesbaden (DE)

(73) Assignee: WEYLCHEM PERFORMANCE PRODUCTS, GMBH, Wiesbaden (DE)

( * ) Notice: Subject to any disclaimer, the term of this patent is extended or adjusted under 35 U.S.C. 154(b) by 0 days.

(21) Appl. No.: 16/990,496

(22) Filed: Aug. 11, 2020

(65) Prior Publication Data

US 2021/0053904 A1 Feb. 25, 2021

(30) Foreign Application Priority Data

Aug. 24, 2019 (DE) ............. 10 2019 005 969.7

(51) Int. Cl.
| | |
|---|---|
| *C07C 69/604* | (2006.01) |
| *C02F 5/10* | (2006.01) |
| *C07C 67/08* | (2006.01) |
| *C09K 8/584* | (2006.01) |
| *C11D 1/08* | (2006.01) |
| *C11D 11/00* | (2006.01) |

(52) U.S. Cl.
CPC ............. *C07C 69/604* (2013.01); *C02F 5/10* (2013.01); *C07C 67/08* (2013.01); *C09K 8/584* (2013.01); *C11D 1/08* (2013.01); *C11D 11/0023* (2013.01)

(58) Field of Classification Search
CPC ......... C02F 5/10; C07C 67/08; C07C 69/604; C07C 69/704; C09K 8/584; C11D 11/0023; C11D 1/08
See application file for complete search history.

(56) References Cited

U.S. PATENT DOCUMENTS

| 3,563,903 A | 2/1971 | Schmadel et al. | |
|---|---|---|---|
| 5,508,394 A | 4/1996 | Kappes | |
| 2002/0082446 A1* | 6/2002 | Ruggieri | C07C 67/08 560/263 |
| 2012/0020906 A1* | 1/2012 | Banowski | A61Q 15/00 424/65 |
| 2012/0103790 A1 | 5/2012 | Krull et al. | |
| 2016/0368945 A1* | 12/2016 | Han | C07K 5/06139 |
| 2020/0172838 A1 | 6/2020 | Barreleiro et al. | |

FOREIGN PATENT DOCUMENTS

| CN | 109293505 A | 2/2019 |
|---|---|---|
| DE | 1617122 A1 | 2/1971 |
| DE | 102009002097 A1 | 10/2010 |
| WO | 9216493 A1 | 10/1992 |
| WO | 2011000463 A2 | 1/2011 |
| WO | 2018210442 A1 | 11/2018 |
| WO | 2019157350 A2 | 8/2019 |
| WO | 2019158409 A1 | 8/2019 |
| WO | WO2019157350 | * 8/2019 |

OTHER PUBLICATIONS

STN Apr. 25, 2018 (Year: 2018).*
A.T. Naeini et al., Nanomedicine, 6(4), pp. 556-562 (2010) copolymers of poly(citric acid) and poly(ethylene glycol) blocks as biocompatible hybrid materials for nanomedicine; abstract, only, included.
M. Memarizadh et al., Environmental Science: Processes & Impacts, 2014, 16, 2380-2389.
Biomaterials 31(34), p. 9092-9105 (2010), D. Gyawali et al.
B. Tisserat et al., J. Polym. Environ (2012), 20:291-298.
B. Tisserat et al., J. of Applied Polymer Science, vol. 125, 3429-3437 (2012).
European Search Report dated Dec. 16, 2020.

(Continued)

*Primary Examiner* — Yevgeny Valenrod
*Assistant Examiner* — Blaine G Doletski
(74) *Attorney, Agent, or Firm* — Michael Ferrell

(57) ABSTRACT

Disclosed are compounds of formula (I)

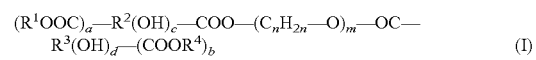

(I)

wherein $R^1$ and $R^4$ independently of one another are hydrogen, a metal cation, an ammonium cation, $C_1$-$C_6$-alkyl, cycloalkyl with three to nine ring carbon atoms, aryl with five to ten ring carbon atoms, aryl that is substituted with one or two alkyl groups, aryl that is connected via an alkylene group with the carboxyl group, —$(C_nH_{2n}$—O$)_m$—H or —O—$R^2(COOR1)_{a+1}$, $R^2$ and $R^3$ independently of one another are aliphatic hydrocarbon residues with one to eight carbon atoms, a and b independently of one another are integers from 1 to 4, c is an integer from 0 to 4, d is an integer from 1 to 4, n is 2, 3 or 4, and m is 1, 2, 3 or 4, with the proviso that $R^1$ and $R^4$ may be different within a molecule within the given definitions.

These compounds are characterized by a very good complexation power for metal cations and can be used in detergents and cleaning agents, in oil extraction and for water softening.

18 Claims, No Drawings

(56) References Cited

OTHER PUBLICATIONS

Journal of Organic Chemistry, Jan. 1, 1989, "Studies on the Mechanism of the Asymmetric Epoxidation: A Ligand Variation Approach", Carlier et al., pp. 4016-4018.
Journal of the American Chemical Society, Oct. 12, 2012, "A Tetradentate Ligand for the Enantioselective Ti(IV)-Promoted Oxidation of Sulfides to Sulfoxides: Origin of Enantioselectivity", Newhouse et al., Bd. 34, Nr. 42, pp. 17354-17357.
Monatshefte fur Cheme Chemical Monthly, Aug. 23, 2004, "Hexafluoroacetone as a Protecting and Activating Reagent. Regioselective Esterification of Aspartic, Malic, and Thiomalic Acid", Pumpor et al., Bd. 135, N. 11, pp. 1427-1443.

* cited by examiner

HYDROXY CARBOXYLIC ACID ESTERS, MANUFACTURING PROCESS THEREOF AND USE THEREOF

CLAIM FOR PRIORITY

This application is based on German Application No. 102019005969.7 filed Aug. 24, 2019, the priority of which is hereby claimed and the disclosure of which is incorporated herein by reference.

TECHNICAL FIELD

The invention relates to new hydroxycarboxylic acid esters derived from aliphatic hydroxycarboxylic acids and from alkylene glycols. These compounds are excellent complexing agents and can be used in a wide variety of fields, for example in detergents and cleaning agents, in oil extraction or for water softening.

BACKGROUND

Polymeric hydroxycarboxylic acid esters, such as polymeric esters of citric acid, are known from the literature and can be prepared by a condensation reaction of the hydroxycarboxylic acid with mono- or polyvalent alcohols. The esterification reaction is carried out by heating the starting components, wherein usually oligomers or polymers with undefined chain length form. There is also a risk of decomposition of the hydroxycarboxylic acid during the reaction, so that uncontrolled by-products are formed, which in turn react with the components of the reaction mixture. For example, citric acid decomposes easily at its melting point with the loss of a COOH group and therefore polyesters with reproducible chain length are difficult to obtain.

From WO 2011/000463 A2 a process for the production of esters of aliphatic carboxylic acids is known. In this process a reaction mixture of aliphatic carboxylic acids and of mono- or polyvalent alcohols is heated by means of microwave radiation for a very short time to very high temperatures far above 100° C. The process provides almost quantitative yields and practically no by-products are generated. Citric acid is mentioned as an example of aliphatic carboxylic acid.

CN 109293505 describes a method for the conversion of lemon juice and hydrochloric acid under the influence of microwave radiation. In this document it is alleged that ethylene glycol citrate is produced by this process. However, it is not disclosed whether ethylene glycol is present during the conversion and when and how ethylene glycol was introduced into the reaction mixture. In addition, the acidified lemon juice is exposed to microwave radiation in a closed container for more than an hour. Under such conditions, a partial decomposition or polymerization of the reactants is to be assumed.

From WO 2019/158409 A1 a method for the production of surface-active condensates of citric acid is known. The obtained products have at least one hydrophobic structural element, which represents a hydrocarbon group with at least eight carbon atoms.

Polymeric citric acids are already known from the literature for a number of applications.

Yuzeng Zao et al. describe in Desalination, Vol. 392, pp. 1-7 (2016) (https://www.sciencedirect.com/science/article/pii/S0011916416301813) the inhibition of the formation of calcium sulfate deposits by using poly(citric acid) derivatives. The applied products have a high polymerization degree and numerous citric acid units.

A. T. Naeini et al. disclose in Nanomedicine, 6(4), pp. 556-562 (2010) copolymers of poly(citric acid) and poly (ethylene glycol) blocks as biocompatible hybrid materials for nanomedicine.

N. Memarizadh et al. describe in Environmental Science: Processes & Impacts, 2014, 16, 2380-2389 supramolecular systems of linear dendritic copolymers and indoxacarb as biodegradable and efficient nanopesticides. As copolymers, dendritic block copolymers of polyethylene glycol and polycitric acid are used.

In Biomaterials 31(34), p. 9092-9105 (2010), D. Gyawali et al. describe in situ curable and biodegradable polymers for the production of cell cultures. The proposed polymers derive from polyethylene glycol, maleic acid and citric acid and tend to develop hydrogels.

B. Tisserat et al. describe in J. Polym. Environ (2012), 20: 291-298 analytical methods for characterizing foams of poly (glycerol citrate) produced by the action of microwave radiation. In the production of the polymers, equimolar amounts of citric acid and glycerol are used, resulting in polymers with high molecular weight.

B. Tisserat et al. describe in J. of Applied Polymer Science, Vol. 125, 3429-3437 (2012) the synthesis of polyesters derived from citric acid and glycerol. For the production of polyesters, the starting materials are provided in different proportions and then heated, using various heating methods, including the action of microwave radiation. Depending on the heating method used and the ratios of the starting materials, different products are obtained, which accumulate as foam, gel or liquid.

WO 92/16493 A1 describes citric acid esters of polyhydroxy compounds having at least three hydroxy groups, such as polyglycerol or sugar alcohols, and their use in detergents and cleaning agents. The compounds can enhance the effect of other detergent additives.

From DE 1,617,122 A water-soluble salts of polyesters comprising free carboxyl groups are known, whose acid components consist of a tri- or tetracarboxylic acid residue and whose alcohol components derive from compounds with two aliphatic hydroxyl groups. For example, polyesters derived from citric acid and ethylene glycol are described. These are highly molecular weight resins that dissolve in alkaline washing liquors. These agents facilitate the washing process and increase the whiteness of the laundry.

Accordingly, from the prior art esters of aliphatic hydroxycarbonic acids and various alcohols are known, for example polyesters derived from citric acid and glycerol or other polyols. Molecules with different chain lengths have already been described, which can include, for example, two units of citric acid up to more than one hundred acid units.

SUMMARY OF INVENTION

For the preparation of esters of aliphatic hydroxycarboxylic acids, condensation reactions in various solvents were carried out, for example in water, glycerol, propylene glycol and ethylene glycol. Surprisingly it was found, that esters prepared from hydroxycarboxylic acids and alkylene glycols or polyalkylene glycols of low condensation degree by a exposure with a high temperature pulse are excellent as complexing agents suitable for different cations. For example, an ester derived from ethylene glycol and citric acid, which has a total of few units of citric acid, shows an excellent tendency to complexation while an ester derived from glycerol and citric acid, which has also a total of a few citric acid units, has no tendency for complex formation.

An object of the present invention is the provision of chemical compounds, which deviate from easily accessible starting materials, preferably from starting materials of biological origin and which have an excellent complex-forming tendency.

The present invention relates to compounds of formula (I)

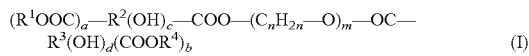

(I)

wherein $R^1$ and $R^4$ independently of one another are hydrogen, a metal cation, an ammonium cation, $C_1$-$C_6$-alkyl, cycloalkyl with three to nine ring carbon atoms, aryl with five to ten ring carbon atoms, aryl that is substituted with one or two alkyl groups, aryl that is connected via an alkylene group with the carboxyl group, $-(C_nH_{2n}-O)_m-H$ or $-O-R^2(COOR1)_{a+1}$, $R^2$ and $R^3$ independently of one another are aliphatic hydrocarbon groups with one to eight, preferably of two to four carbon atoms, a and b independently of one another are integers of 1 to 4, preferably 1 to 3, c is an integer from 0 to 4, preferably 1 to 4, in particular 1 or 2 and most preferred 1, d is an integer from 1 to 4, preferably 1 or 2 and most preferred 1, n is 2, 3 or 4, preferably 2 or 3 and in particular 2, and m is 1, 2, 3 or 4, with the proviso that R' and $R^4$ may be different within a molecule within the given definitions.

Compounds of formula (I) may be also represented by formula (Ia)

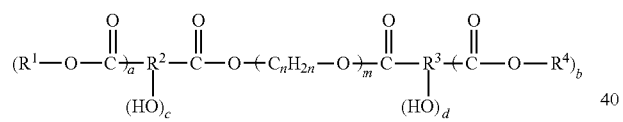

(Ia)

wherein $R^1$, $R^2$, $R^3$, $R^4$, a, b, c, d, m and n have the meaning defined above.

By NMR analysis it can be concluded that in the condensation reaction mediated by pulse-shaped temperature increase, for example by microwave radiation, molecules with a few hydroxycarboxylic acid are formed, for example molecules with 2 or 3 citric acid units. The hydroxycarboxylic acid units, for example the citric acid units, are bound via ester bonds to units that derive from alkylene glycols or from di- to tri-alkylene glycols that are use as solvent. This results in low-molecular weight compounds and in no polymers.

DETAILED DESCRIPTION

Hydroxycarboxylic acids when reacted with alcohols other than (poly)alkylene glycols, for example in the reaction with glycerol, showed a very high solution viscosity or brown coloration, and in addition, the resulting products showed no or only a low complexing tendency.

Polyesters containing a larger number of hydroxycarboxylic acid units and alcohol units often have too high viscosities and are therefore not free-flowing and not pumpable. These products are usually produced by heating with conventional sources and are not suitable as complexing agents.

The compounds of formula (I) according to the invention are often present as liquids, in particular as transparent liquids with a viscosity at 25° C. of at least 100 mPas, measured with the rotary viscosimeter (Brookfield viscosimeter).

The compounds of formula (I) according to the invention are generally available as mixtures of substances. The preferred substance mixtures derived from citric acid and ethylene glycol contain, for example, ethylene glycol di-citric acid ester of the following formula

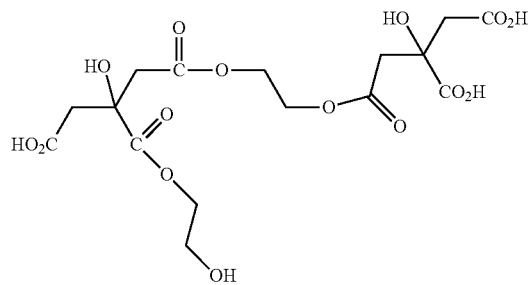 [SMILES: O=C(O)CC(O)(CC(=O)OCCOC(=O)CC(O)(CC(=O)O)C(=O)OCCO)C(=O)O]

This ester is excellently suited for complexing with metal ions, especially with alkaline earth metal ions. A complex with calcium is shown below

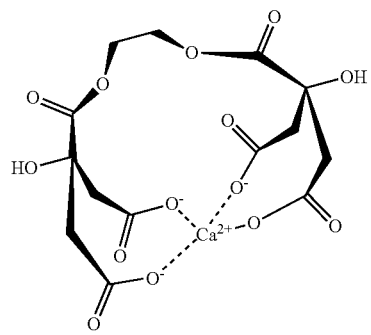

However, there are also other citric acid esters in the mixture, for example compounds with a free carboxyl group instead of the ethylene glycol ester group $-COO-CH_2-CH_2-OH$ or compounds in which further citric acid units are bonded to the hydroxyl group of the alkylene glycol unit via their carboxyl group.

In addition, the mixtures may also contain small proportions of non-reacted starting materials, e.g. free diols and/or hydroxycarboxylic acids or optionally carboxylic acids.

The mixtures containing different polyesters of formula (I) are usually liquid at 25° C. The viscosity of these mixtures is preferably 0.1 to 10,000 mPa*s at 20° C., measured with the Brookfield viscosimeter (spindles 1 to 7, depending on the viscosity range; shear speed 5 revolutions/minute), preferably 1 to 7500 mPa*s and particularly preferred 100 to 2000 mPas.

The polyesters of the invention are prepared by reaction of aliphatic hydroxycarboxylic acids with selected aliphatic (poly)alkylene glycols. The latter are alkylene glycols with two, three or four carbon atoms or polyalkylene glycols with two, three or four repeating units thereof. these compounds generally have the following structure

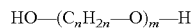

wherein n and m have the meaning defined above.

Preferably, ethylene glycols or propylene glycols are used, i.e. compounds of the above formula in which n is 2 or 3.

Particularly preferred (poly) ethylene glycols are used, i.e. compounds of the above formula in which n is 2.

Particularly preferred, ethylene glycol or diethylene glycol are used, i.e. compounds of the above formula in which n is 2 and m is 1 or 2.

Very preferred ethylene glycol is used, i.e. a compound of the above formula in which n is 2 and m means 1.

Compounds of the formula (I), in which n is 2 or 3, and m is 1 or 2 are preferred. These compounds are derived from ethylene glycol, propylene glycol, di-ethylene glycol or di-propylene glycol.

Particularly preferred are compounds of formula (I), where n is 2, and m is 1. These compounds are derived from ethylene glycol.

The aliphatic hydroxycarboxylic acids used in the preparation of the compounds of formula (I) of the invention include arbitrary types. These can be aliphatic hydroxycarboxylic acids with two, three or four or five carboxyl groups. The aliphatic hydroxycarboxylic acids may have one to four hydroxyl groups. A hydroxyl group may be located with a carboxyl group on a common carbon atom, or the hydroxyl group is in alpha, beta or other position to a carboxyl group. The carboxyl groups are generally located on different carbon atoms of the aliphatic residue. If several hydroxyl groups are present, they are located on different carbon atoms of the aliphatic residue. The aliphatic residue usually has one to eight, preferably two to four carbon atoms.

Preferably, compounds of formula (I) derive from malic acid, lactic acid, tartronic acid, tartaric acid, isocitric acid, citric acid, acetyl citric acid, tartaric acid or mucic acid, in particular from isocitric acid or citric acid, and very preferred from citric acid.

In the preparation of the compounds of formula (I) also aliphatic hydroxycarboxylic acids may optionally become combined with aliphatic carboxylic acids. Instead of the aliphatic hydroxycarboxylic acids or the aliphatic carboxylic acids, their ester-forming derivatives, such as esters, anhydrides, halogenides or their salts, can also be used.

Preferably, in the preparation of the compounds of formula (I) exclusively one or more aliphatic hydroxycarboxylic acids and/or their reactive derivatives and/or their salts are used.

Carboxylic acids optionally used in the preparation of the compounds of the formula (I) of the invention include arbitrary types. These may be aliphatic carboxylic acids with two, three or four or five carboxyl groups. The carboxyl groups are generally located on different carbon atoms of the aliphatic residue. The aliphatic residue usually has one to eight, preferably two to four carbon atoms.

Examples of aliphatic carboxylic acids are oxalic acid, malonic acid, succinic acid, glutaric acid, adipic acid, pimelic acid, suberic acid, azelaic acid, sebacic acid, carballylic acid, butane-1,2,4-tricarboxylic acid or octric acid. In the preparation of the compounds of formula (I) different aliphatic carboxylic acids can be used in combination with aliphatic hydroxycarboxylic acids or with derivatives of aliphatic hydroxycarboxylic acids, such as their esters or their salts.

The residues $R^1$ and $R^4$ can mean alkyl. These are alkyl groups with one to six carbon atoms, which can be straight chain or branched. Methyl and ethyl are preferred.

The residues $R^1$ and $R^4$ can mean cycloalkyl. These are cycloalkyl groups with three to nine ring carbon atoms, preferably five to seven ring carbon atoms. Particularly preferred is cyclohexyl.

The residues $R^1$ and $R^4$ can mean aryl. These are aromatic hydrocarbon residues with five to ten ring carbon atoms. Phenyl is preferred.

The residues $R^1$ and $R^4$ can mean alkylaryl. These are aryl groups that are substituted with one or two alkyl groups. Tolyl is preferred.

The residues $R^1$ and $R^4$ can mean aralkyl. These are aryl groups that are connected to the carboxyl group via an alkylene group. Benzyl is preferred.

Preferred residues $R^1$ and $R^4$ are hydrogen, metal cations, ammonium cations or residues of the formula $-(C_nH_{2n}-O)_m-H$.

In particular, residues $R^1$ and $R^4$ are hydrogen, cations of alkali metals, cations of alkaline earth metals, quaternary ammonium cations or residues of the formula $-(C_nH_{2n}-O)_m-H$, in particular residues of the formula $-C_2H_4-OH$.

Residues $R^2$ and $R^3$ are aliphatic hydrocarbon residues with one to eight, preferably two to four carbon atoms. $R^2$ and $R^3$ can be straight-chain or branched. The valency of a residue $R^2$, thus the number of covalent bonds that connect this residue with the other groups of the molecule, is a+c+1. Depending on the size of indices a and c, the valency of $R^2$ can therefore be between 2 and 9. The valency of a residue $R^3$ is b+d+1. Thus, depending on the size of indexes b and d, the valency of $R^3$ can be between 3 and 9. Not all of the generally possible residues $R^2$ or $R^3$ can have a valency in the range of 2 to 9 or in the range of 3 to 9, since due to the tetravalent carbon atom, the number of possible free valences in individual cases may be smaller. A residue $R^2$ with e.g. only one carbon atom can therefore only assume values in the range between 2 and 4. The skilled artisan is aware of this context.

Preferred are divalent residues $R^2$ with the formula $-O_oH_{2o}-$ or trivalent residues $R^2$ with the formula $-C_pH_{2p-1}<$ or tetravalent residues $R^2$ with the formula $>C_qH_{2q-2}<$, wherein o is an integer of 2 to 4, preferably from 2 to 3 and particularly preferred 2, p is an integer of 1 to 4, preferably from 1 to 3 and more preferred 1 or 2, and q is an integer of 2 to 4, preferably from 2 to 3 and more preferred 3.

Particularly preferred are compounds of formula (I), in which $R^2$ and $R^3$ are residues that derive from malic acid, lactic acid, tartronic acid, tartaric acid, isocitric acid or citric acid after removal of the carboxyl groups and the hydroxy group.

These especially preferred residues $R^2$ and $R^3$ have structures of formulae (Ib), (Ic), (Id), (Ie), (If) or (Ig)

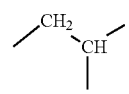

(Ib)

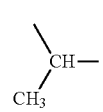

(Ic)

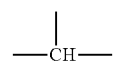

(Id)

-continued (Ie)

$$\diagup^{CH}\diagdown_{CH}\diagup$$

(If)

$$\diagup^{CH}\diagdown_{CH}\diagup^{CH_2}\diagdown$$

(Ig)

$$\diagup^{CH_2}\diagdown\diagup^{CH_2}\diagdown_{CH_2}$$

Particularly preferred are compounds of formula (I), in which a and b are 2, $R^2$ and $R^3$ are aliphatic hydrocarbon groups having three carbon atoms, in particular aliphatic hydrocarbon residues derived from citric acid, and $R^1$ and $R^4$ are hydrogen, cations of alkali metals, cations of alkaline earth metals, quarternary ammonium cations or residues of the formula —$(C_nH_{2n}-O)_m$—H.

Particularly preferred is the compound of the following formula (II) or their alkali or alkaline earth salts or partial neutralisates thereof $$HO-C(CH_2-COOH)_2-COO-O_2H_4-OOC-COH-(CH_2COOH)_2 \quad (II).$$

Compounds of formula (II) may be also represented by formula (IIa)

(IIa)

$$HO-\underset{\underset{O}{\|}}{C}-\underset{\underset{HO}{|}}{C}H_2-\underset{\underset{HO}{|}}{C}-\underset{\underset{O}{\|}}{C}-O-C_2H_4-O-\underset{\underset{O}{\|}}{C}-\underset{\underset{HO}{|}}{C}-\underset{CH_2}{\overset{CH_2}{|}}-\underset{\underset{O}{\|}}{C}-OH$$

In addition, mixtures containing different compounds of the formula (I), which are liquid at 25° C. are particularly preferred.

Furthermore, compounds of formula (I) having a residue of the formula $(R^1OOC)_a$—$R^2(OH)$—COO— and a residue of the formula $(R^4OOC)_b$—$R^3(OH)COO$— are also preferred, wherein these residues have the same meaning.

The compounds of formula (I) can be prepared by esterification of aliphatic hydroxycarboxylic acids or their ester-forming derivatives, such as their alkyl esters, with selected diols at elevated temperature, wherein the temperature increase in the reaction mixture must be pulse-like but temperature controlled. Under these conditions, only small molecules are formed and no polymerization or decomposition of the components used takes place. Optionally the reaction mixture may additionally contain aliphatic carboxylic acids or their ester-forming derivatives.

The invention therefore also relates to a method for preparing the compounds of formula (I) with the measures:
  (i) provision of hydroxycarboxylic acids of formula (V) or their ester-forming derivatives, such as their alkyl esters, and optionally of carboxylic acids or hydroxycarboxylic acids of formula (IV) or their ester-forming derivatives, such as their alkyl esters, and of alkylene glycol of formula (VI)

$$(R^1OOC)_a-R^2(OH)_c-COOR^1 \quad (IV)$$

$$R^4OOC-R^3(OH)_d(COOR^4)_b \quad (V)$$

$$OH-(C_nH_{2n}-O)_m-H \quad (VI)$$

wherein $R^1$, $R^2$, $R^3$, $R^4$, a, b, c, d, n and m have the meaning defined above,
  (ii) heating the mixture obtained in step (i) to at least 90° C. for a period of 0.1 milliseconds to 60 minutes, and
  (iii) cooling the product mixture obtained in step (ii) to 25° C. or below within a period between 1 second and 60 minutes.

The supply of the required heating power can be carried out by any device which is able to enter briefly high amounts of heating power into the reaction mixture. It is important to limit the reaction temperature to such values in such a way that decomposition of the reactants is avoided. Examples of suitable devices are heat exchangers, in particular recuperators, or electromagnetic radiation in the microwave band.

Known types can be used as recuperators. Examples of these are plate heat exchangers, capillary heat exchangers, microreactors, spiral tube heat exchangers, tube bundle heat exchangers, U-pipe heat exchangers, jacket tube heat exchangers, heat registers or countercurrent heat exchangers.

Preferably, the reaction mixture is charged in the heating zone with high heating power by heating with electromagnetic radiation in the microwave band or with a heat exchanger.

Particularly preferred, the heating zone is designed in the form of a pressure-resistant, microwave-transparent pipe, which is located in an appropriately dimensioned cavity resonator, which is able to generate an electromagnetic field, preferably in the microwave band, of appropriate field strength, with the aid of which the reaction material is heated by dielectric heating mechanisms.

The used electromagnetic radiation preferably has a frequency in the range of 300 MHz to 30 GHz, in particular a frequency of 915 MHz, 2.45 GHz or 5.8 GHz.

Due to the short-term exposure of high temperatures to the reaction mixture, esterification and transesterification reactions take place in this mixture very fast and simultaneously. In this case, most of the hydroxycarboxylic acids and diols present are esterified, wherein in the case of hydroxycarboxylic acids with several carboxyl groups often a part of the carboxyl groups remains unesterified.

Preferred is a method in which the heating in step ii) is carried out by irradiation of microwave radiation.

The reaction temperature in step (ii) is generally in the range between 90 and 190° C., preferably from 120 to 180° C. and most preferred from 140 to 160° C.

Particularly preferred is a method in which the mixture in step (ii) is heated to a temperature between 140 and 160° C. and in which the time period of heating is from 1 to 120 seconds.

The method according to the invention can be carried out batchwise or preferably continuously.

In the implementation of the method according to the invention, the alkylene glycols are preferably used in molar excess to the hydroxycarboxylic acid.

Usually, the molar ratio of hydroxycarboxylic acid to alkylene glycol is 1:10 to 10:1, preferably 5:1 to 1:5, and particularly preferred 1:1 to 1:3.

The method according to the invention can be carried out in different reaction mixtures. Examples are emulsions or solutions. Preferably, the method according to the invention is carried out in solution. In the method of the invention the reaction mixture according to process step i) contains compounds of formula (V) and optionally of formula (IV) or their ester-forming derivatives and compounds of formula (VI).

As solvents, all liquids in which the reactants dissolve and which are essentially inert under the reaction conditions are possible. Examples thereof are aprotic polar organic solvents.

In a preferred embodiment, the used alkylene glycol serves simultaneously as a solvent for the resulting oligoester.

The method of the invention can be carried out with or without the use of esterification or transesterification catalysts. Examples of esterification or transesterification catalysts are acidic catalysts or their mixtures. These may be inorganic, organometallic and/or organic acidic compounds. As acidic inorganic catalysts within the meaning of the present invention, mineral acids can be used, for example hydrochloric acid, boric acid, nitric acid, sulfuric acid, phosphoric acid, phosphonic acid or hypophosphoric acid; in addition, acidic salts can be used, such as aluminium sulfate hydrate, alum, acidic silica gel or acidic aluminium hydroxide. Other acidic inorganic catalysts are, for example, aluminium compounds of the general formula $Al(OR)_3$ and titanates of the general formula $Ti(OR)_4$, wherein the residues R may be equal or different and are independently selected from $C_1$-$C_{10}$ alkyl residues, for example methyl, ethyl, n-propyl, iso-propyl, n-butyl, iso-butyl, sec.-butyl, tert.-butyl, n-pentyl, iso-pentyl, sec.-pentyl, neo-pentyl, 1,2-dimethylpropyl, iso-amyl, n-hexyl, sec.-hexyl, n-heptyl, n-octyl, 2-ethylhexy, n-nonyl or n-decyl, $C_3$-$C_{12}$ cycloalkyl residues, such as cyclopropyl, cyclobutyl, cyclopentyl, cyclohexyl, cycloheptyl, cyclooctyl, cyclononyl, cyclodecyl, cycloundecyl and cyclododecyl; preferably cyclopentyl, cyclohexyl and cycloheptyl. Preferably, the residues R in $Al(OR)_3$ and $Ti(OR)_4$ respectively are equal and selected from isopropyl, butyl and 2-ethylhexyl.

Preferred acidic organometallic catalysts are selected from dialkyl tin oxides $(R^3)_2SnO$, wherein $R^3$ is defined as above. A particularly preferred representative for acidic organometallic catalysts is di-n-butyltin oxide, which is commercially available as so-called oxo-tin or as Fascat<(R)>brands.

Preferred acidic catalysts are organic compounds that contain acidic groups, for example phosphate groups, phosphonic acid groups, sulfonic acid groups, sulfate groups or carboxylic acid groups. Particularly preferred sulfonic acids contain at least one sulfonic acid group and at least one saturated or unsaturated, linear, branched and/or cyclic hydrocarbon residue with 1 to 40 C-atoms and preferably with 1 to 24 C-atoms. In particular, aromatic sulfonic acids and especially alkylaromatic monosulfonic acids with one or more $C_1$-$C_{25}$-alkyl residues and in particular those with $C_1$-$C_{22}$-alkyl residues are preferred.

Preferred examples are methane sulfonic acid, butane sulfonic acid, benzene sulfonic acid, p-toluene sulfonic acid, xylene sulfonic acid, 2-mesitylene sulfonic acid, 4-ethylbenzene sulfonic acid, isopropyl benzene sulfonic acid, 4-butylbenzene sulfonic acid, 4-octylbenzene-sulfonic acid, dodecylbenzene sulfonic acid, didodecylbenzene sulfonic acid, naphthalene sulfonic acid.

Particularly preferred for carrying out the method of the invention are boric acid, phosphoric acid, polyphosphoric acid and polystyrene sulfonic acids.

In particular, titanates of the general formula $Ti(OR)_4$ and specifically titanium tetrabutylate and titanium tetraisopropylate are preferred.

In a further embodiment, acidic and solid catalysts are used in the inventive method. Examples include zeolites, silica gel, acidic layered silicates, such as montmorillonite, and organic ion exchangers.

Preferably, the method according to the invention is carried out without the use of esterification or transesterification catalysts.

The catalysts are typically used in amounts of up to 10 wt. %, based on the total mass of the reaction mixture, preferably in amounts of 0.01 to 10 wt.-% and particularly preferred from 0.02 to 2 wt.-%.

The reaction mixture is guided through a reactor. The reaction mixture in a heating zone experiences a strong heating due to the supply of heating power. This can be performed by physical contact with a hotter wall by heat transfer or by interaction of polar or ionic molecules with electromagnetic fields, for example with wavelengths in the centimeter range (microwave)

According to the invention, the reaction mixture in the heating zone is charged for a period of up to 60 minutes, typically from 0.1 milliseconds to 60 minutes, preferably from 1 second to 10 minutes, and most preferred from 1 second to 2 minutes with a sufficiently high heating power. The reaction mixture experiences a strong temperature increase and has a temperature between 90° C. and 190° C. when leaving the heating zone, preferably between 120° C. and 180° C. and particularly preferred between 140° C. and 160° C., measured by temperature sensor PT100 immediately after leaving the heating zone.

The reaction mixture may be present in the reactor under vacuum, atmospheric pressure or in particular under overpressure. Preferably, the pressure in the reactor is 0 to 1000 bar absolute, more preferred 1 mbar to 200 bar, absolute, particularly preferred 50 mbar to 20 bar absolute and most preferably between 1 and 20 bar absolute. The pressure in the reactor shall be chosen in particular in such a manner that both the reaction mixture and the condensates in the reactor are present in liquid state during the reaction. In this variant, the reaction mixture is efficiently heated in the reaction zone, especially in the case that electromagnetic radiation, such as microwave radiation, is used for this purpose.

The residence time in the heating zone is adjusted by the selection of a suitable flow-speed of the reaction mixture through this zone. Another preferred option for adjusting the residence time according to the invention is a suitable selection of the apparatus size.

In one embodiment of the method according to the invention, the heating zone of the reactor is affiliated to a dwell line. The product mixture resulting from the reaction mixture may remain after the heating zone in this dwell line for a residence time of up to 60 minutes, preferably from 1 to 600 seconds, particularly preferred from 1 to 120 seconds.

The feeding of the required heating power in the heating zone can be carried out by any device which is able to add short-term high amounts of heating power to the reaction mixture. Examples of suitable devices have already been described above.

Due to the short-term exposure of high temperatures and pressure on the reaction mixture, esterification and optionally transesterification reactions take place very rapidly therein. A part of the alcohols and carboxylic acids present is converted into carboxylic acid esters with comparatively low molecular weight and—depending on the starting substance—alcohols and/or reaction water are released.

The cooling of the hot product mixture in step iii) may take place in the dwell line and/or in a cooling section downstream of the dwell zone or the reaction zone. Preferably, the hot product mixture is cooled rapidly to avoid further conversions.

The obtained product mixture can be combined as such without further processing with other substances or it can be worked-up before further processing.

According to step iii) as a work-up, for example, drying and/or neutralization of the product mixture and/or separation of solid components can be carried out.

The optionally worked-up product mixture can be further processed by applying it to a solid carrier and/or by granulation together with other substances.

Experiments have shown that the compounds of formula (I) according to the invention are suitable as exceptionally good complexing agents for metal cations, in particular for alkaline earth metal cations, such as $Mg^{2+}$ and $Ca^{2+}$.

The invention therefore also relates to the use of the compounds of formula (I) as complexing agents for metal cations.

The invention also relates to the use of the compounds of formula (I) as complexing agents in detergents and cleaning agents, in oil extraction or for water softening.

In addition, the invention relates to detergents and cleaning agents containing compounds of formula (I).

As detergents and cleaning agents, in particular, agents for cleaning of dishes are possible, especially those that are suitable for use in automatic dishwashers.

For use in detergents and cleaning agents, the compounds of formula (I) are usually used in the form of granules in combination with other components of detergents and cleaning agents.

The performance of bleach in detergents and cleaning agents can be significantly increased if a peroxygen compound used as bleaching agent is brought into contact with a combination of bleach catalyst and bleach activator. Here, the bleaching effect of the catalyst is effectively supported by the peroxycarboxylic acid formed from the activator. At the same time, the peroxycarboxylic acid contributes significantly to the germ-killing on the goods to be cleaned, improves the smell of the washing liquor and prevents the formation of a biofilm in the washing machine or dishwasher. The combination of bleach catalysts and/or bleach activators is therefore useful for increasing the bleaching effect and ensuring hygiene in the use of bleach in detergents and cleaning agents.

Preferred washing and cleaning agents according to the invention, in particular the agents for cleaning dishes, contain the compounds of the formula (I) according to the invention in quantities between 0.1 and 10 wt.-%, preferably in quantities between 0.2 and 8 wt.-% and especially preferred in quantities between 0.5 and 6 wt.-%. The percentages refer to the total weight of the detergent and cleaning agent.

The washing and cleaning agents according to the invention, which may be present as granules, powder- or tablet-shaped solids but also in liquid or pasty form, can contain in principle all known ingredients used in such agents.

The washing and cleaning agents of the invention may in particular contain builder substances, peroxygen compounds, enzymes, alkali carriers, surface-active agents, pH regulators, organic solvents and other adjuvants, such as glass corrosion inhibitors, silver corrosion inhibitors and foam regulators. The granules of the invention are suitable for use in phosphate-containing as well as in particular in phosphate-free formulations.

Particularly preferred detergents and cleaning agents, in particular agents for the cleaning of dishes, contain
(i) 5 to 65 wt.-%, preferably 10 to 60 wt. % of a water-soluble builder component,
(ii) 5 to 20 wt.-%, preferably 8 to 15 wt.-%, of a peroxygen compound,
(iii) 0.5 to 25 wt.-% of a compound of the formula (I) according to the invention, and
(iv) 0 to 50 wt.-% of additional additives such as enzymes, alkali carriers, surface-active agents, pH regulators, organic solvents or other adjuvants, such as glass corrosion inhibitors, silver corrosion inhibitors and foam regulators, each based on the total weight of the detergent and cleaning agent.

Such an agent is in particular of low alkalinity, i.e. its 1 wt.-% aqueous solution has a pH in the range of 8 to 11.5 and preferably from 8 to 11.

Possible ingredients of detergents and cleaning agents are adequately described in the patent literature, for example in WO 2018/210442 A1.

Examples of preferred water-soluble builder components in the washing and cleaning agents of the invention are organic polymers of native or synthetic origin of the type of polycarboxylates, which act in particular in hard water regions as co-builders. For example, polyacrylic acids and copolymers of maleic acid anhydride and acrylic acid as well as the sodium salts of these polymer are considered. Commercially available products include Sokalan® CP 5, CP 10 and PA 30 from BASF. The polymers of native origin that can be used as co-builders include, for example, oxidized starch and polyaminoacids such as polyglutamic acid or polyasparagic acid. Other possible water-soluble builder components are naturally occurring hydroxycarboxylic acids, such as mono-, dihydroxy succinic acid, alpha-hydroxypropionic acid and gluconic acid. The preferred organic water-soluble builder components include the salts of citric acid, in particular sodium citrate. Depending on the pH value finally set in the washing and cleaning agents of the invention, the acids corresponding to the mentioned co-builder salts may also be present. Particularly preferred builder components in phosphate-free formulations are methylglycindiacetate (MDGA, e.g. Trilon® M, BASF), L-glutamic acid, N,N, (biscarboxymethyl)-tetra sodium salt (GLDA, Dissolvine® DL, Akzo Nobel), sodium polyaspartate (Baypure®, Lanxess) or salts of iminodisuccinic acid (Baypure®, Lanxess).

Examples of preferred peroxygen compounds in the detergents and cleaning agents of the invention are perborates and percarbonates, in particular the corresponding sodium salts of these compounds.

The enzymes optionally contained in the washing and cleaning agents of the invention include proteases, amylases, pullulanases, cutinases and/or lipases. The enzymes used may be adsorbed on carriers and/or embedded in enveloping substances to protect them against premature inactivation. They are typically present in the washing and cleaning agents of the invention in amounts up to 10 wt.-% and preferably in amounts of 0.05 to 5 wt. %, wherein particularly preferably enzymes stabilized against oxidative degradation are used.

Preferably, the washing and cleaning agents according to the invention, in particular the agents for cleaning dishes, contain commonly used alkali carriers, such as alkalisilicates, alkalicarbonates and/or alkali hydrogen carbonates.

Examples of these are given in WO 2018/210442 A1. Alkaline carriers can be present in amounts of up to 50 wt. % and preferably from 5 to 40 wt. % in the detergent and cleaning agents.

Examples of preferred surfactants contained in the detergents and cleaning agents of the invention are anionic surfactants, twitterionic surfactants and preferably weak foaming nonionic surfactants. Their amount can be up to 20 wt.-%, preferably up to 10 wt.-% and particularly preferred in the range of 0.5 to 5 wt.-%, based on the total weight of the detergent and cleaning agent. Examples of surfactants are mentioned in WO 2018/210442 A1.

To set a desired pH-value that is not self-resulting from the mixture of the other components, the washing and cleaning agents of the invention may contain system and environmentally compatible acids, in particular citric acid, acetic acid, tartaric acid, malic acid, lactic acid, glycolic acid, succinic acid, glutaric acid and/or adipic acid, but also mineral acids, in particular sulphuric acid or alkalihydrogen sulfates, or bases, preferably ammonium or alkali hydroxides. These pH-regulators are contained in the washing and cleaning agents according to the invention, in particular in the agents for the cleaning of dishes, of preferably not more than 10 wt.-% and particularly preferred from 0.5 to 6 wt.-%, each based on the total weight of the agent.

Examples of preferred organic solvents contained in the detergents and cleaning agents of the invention are alcohols with 1 to 4 C atoms, in particular methanol, ethanol, isopropanol and tert. butanol, diols with 2 to 4 C atoms, in particular ethylene glycol and propylene glycol, as well as their mixtures and ethers derivable from the mentioned compound classes. Such water-miscible solvents are typically present in the washing and cleaning agents according to the invention in an amount of not more than 20 wt.-% and especially preferred from 1 to 15 wt.-%.

For suppression of glass corrosion during the rinsing process, appropriate inhibitors can be used in the washing and cleaning agents according to the invention, in particular in the agents for cleaning dishes. Particularly advantageous here are crystalline layer-shaped silicates and/or zinc salts. Examples of glass corrosion inhibitors are mentioned in WO 2018/210442 A1.

In a further preferred embodiment, the washing and cleaning agents according to the invention, in particular the agents for cleaning dishes, contain an amount of the crystalline layer-shaped silicate between 0.1 and 20 wt.-%, more preferred between 0.2 to 15 wt.-% and particularly preferred between 0.4 to 10 wt.-%, each based on the total weight of the agent.

In order to effect a silver corrosion protection, silver corrosion inhibitors can be used in the washing and cleaning agents according to the invention, in particular in the agents for the cleaning of dishes. Examples of silver corrosion inhibitors are mentioned in WO 2018/210442 A1.

The washing and cleaning agents according to the invention, in particular the agents for the cleaning of dishes, may contain further ingredients known in the prior art for such agents, for example sequestration agents, electrolytes, additional peroxygen activators, dyes or fragrances, such as perfume oils.

The preparation of the solid detergents and cleaning agents according to the invention, in particular the agents for cleaning dishes, offers no difficulties and can in principle be carried out in a manner known per se, for example by spray drying or granulation, wherein peroxygen compound and granules according to the invention may be added separately later.

Washing and cleaning agents according to the invention in the form of aqueous or other commonly used solvent containing solutions, in particular corresponding agents for the cleaning of dishes, are prepared particularly advantageously by simple mixing of the ingredients, which can be added into an automatic mixer in substance or as a solution.

The washing and cleaning agents according to the invention, in particular the agents for the cleaning of dishes, are preferably available as powdered, granular or tablet-shaped preparations, which are prepared in a known manner, for example by mixing, granulating, roll compaction and/or by spray drying of thermally resilient components and by adding the more sensitive components, which in particular are enzymes, bleaches and bleaching catalysts.

Agents for the machine cleaning of dishes according to the invention can be used in household dishwashers as well as in commercial dishwashers. They may be added by hand or by means of suitable dosing devices. The application concentrations in the cleaning broth are usually about 1 to 8 g/l, preferably 2 to 5 g/l.

A machine rinsing programme is conveniently supplemented and terminated by some intermediate rinse softening swells followed by the cleaning process with clear water and a rinse duct with a common rinse detergent. After drying, when using the dishwashing detergent according to the invention, one gets completely clean and hygienically flawless dishes.

EXAMPLES

In the following examples %-references shall mean % by weight percentage unless explicitly stated otherwise.

Preparation Examples

Example 1: Production of Oligo-Citric Acid Monoethylene Glycol Ester

In a 5 l Büchi agitator autoclave with stirrer, internal thermometer and pressure equalizer, 2.5 kg of citric acid (as monohydrate) were provided and mixed with 6.5 kg of monoethylene glycol and 0.05 kg of sulfuric acid.

The resulting mixture was heated to 80° C., with all reactants completely being in solution. At a working pressure of 15 bar, the reaction solution was continuously pumped through the reaction tube at 5 l/h and exposed to a microwave power output of 1.5 kW, of which 91% was absorbed by the reaction material. The residence time of the reaction mixture in the irradiation zone was about 25 seconds. At the end of the reaction tube, the reaction mixture had a temperature of 155° C. The reaction mixture was cooled to room temperature immediately after leaving the reactor with an intensive heat exchanger.

Example 2 (Comparison): Production of Oligo-Citric Acid-Glycerol Esters

In a 5 l Büchi agitator autoclave with stirrer, internal thermometer and pressure equalizer, 2.5 kg of citric acid (as monohydrate) were provided and mixed with 4.8 kg glycerol and 0.05 kg of methane sulfonic acid.

The resulting mixture was heated to 75° C., with all reactants being completely in solution. At a working pressure of 15 bar, the reaction solution was continuously pumped through the reaction tube at 5 l/h and exposed to a microwave power output of 1.3 kW, of which 94% was absorbed by the reaction material. The residence time of the reaction mixture in the irradiation zone was about 25 seconds. At the end of the reaction tube, the reaction mixture had a temperature of 160° C. The reaction mixture was cooled to room temperature immediately after leaving the reactor with an intensive heat exchanger.

Example 3: Manufacture of Oligo-Citric Acid Monoethylene Glycol Esters without the Use of a Reaction-Accelerating Catalyst In a 5 l Büchi agitator autoclave with stirrer, internal thermometer and pressure equalizer, 2.5 kg of citric acid (as monohydrate) were provided and mixed with 6.5 kg of monoethylene glycol. The addition of a catalyst was dispensed with at this point.

The resulting mixture was heated to 80° C., with all reactants being completely in solution. At a working pressure of 15 bar, the reaction solution was continuously pumped through the reaction tube at 5 l/h and exposed to a microwave power output of 1.5 kW, of which 90% was absorbed by the reaction material. The residence time of the reaction mixture in the irradiation zone was about 25 seconds. At the end of the reaction tube, the reaction mixture had a temperature of 155° C. The reaction mixture was cooled to room temperature immediately after leaving the reactor with an intensive heat exchanger.

Use Examples

The transparent solutions produced according to manufacturing examples 1, 2 and 3 were tested in a dishwashing detergent formulation based on citrate. It was investigated whether the use of these solutions can prevent the deposit of calcium carbonate on glasses and other dishes.

The following table describes the composition of dishwashing detergents used in the tests.

TABLE

| Ingredient | 1 | 2 | 3 | 4 |
|---|---|---|---|---|
| tri-sodium-citrate | 36% | 35% | 35% | 35% |
| sodium carbonate | 30% | 30% | 30% | 30% |
| percarbonate | 15% | 15% | 15% | 15% |
| TAED | 5% | 5% | 5% | 5% |
| PEG1500 | 3% | 3% | 3% | 3% |
| PEG6000 | 2% | 2% | 2% | 2% |
| Sokalan PA25 | 5% | 5% | 5% | 5% |
| Lutensol TO 7 | 1% | 1% | 1% | 1% |
| Protease Blaze 100T | 2% | 2% | 2% | 2% |
| Amylase Stainzyme Evity 121 | 1% | 1% | 1% | 1% |
| Parfume, Dye, etc. | 0% | 0% | 0% | 0% |
| mixture according to preparation example 1 | 0% | 1% | 0% | 0% |
| mixture according to preparation example 2 | 0% | 0% | 1% | 0% |
| mixture according to preparation example 3 | 0% | 0% | 0% | 1% |
| Sum | 100% | 100% | 100% | 100% |

The powder formulations were mixed and were dosed as 20 g portions from the dosing chamber. The liquid mixture from manufacturing example 1 or 2 or 3 was dosed via pipettes on the powder. The pH-value, measured as a 1 wt. % solution in water, was 10.2.

The rinsing performance was measured in a Miele GSL 2 at 55° C. using water with a 21 degree hardness. Three washing programs were passed through each. Long drink glasses by Schott Zwiesel were visually evaluated in a black box in terms of film and stain formation. Ratings from 1 to 10 were assigned (1=worst value; 10=best value). The average value of all ratings was calculated. The results are found in the table below.

TABLE

| Formulation | 1 | 2 | 3 | 4 |
|---|---|---|---|---|
| film- and stain-formation | 5.9 | 6.9 | 5.1 | 7.6 |

The gloss on the glasses had significantly improved when a mixture containing monoethylene glycol-di-citric acid esters produced according to manufacturing examples 1 and 3 was used in the dishwashing detergent formulation.

The gloss on the glasses had not improved when a mixture containing monoglycerol-di-citric acid esters produced according to manufacturing example 2 was used in the dishwashing detergent formulation.

The invention claimed is:

1. A composition comprising two different compounds of formula (I)

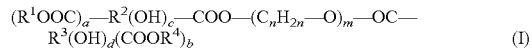

wherein $R^1$ and $R^4$ independently of one another are hydrogen, a metal cation, an ammonium cation, $C_1$-$C_6$-alkyl, cycloalkyl with three to nine ring carbon atoms, aryl with five to ten ring carbon atoms, aryl that is substituted with one or two alkyl groups, aryl that is connected via an alkylene group with the carboxyl group, —$(C_nH_{2n}$—O$)_m$—H or —O—$R^2(COOR^1)_{a+1}$, $R^2$ and $R^3$ independently of one another are aliphatic hydrocarbon residues with one to eight carbon atoms, a and b independently of one another are integers from 1 to 4, c is an integer from 0 to 4, d is an integer from 1 to 4, n is 2, 3 or 4, and m is 1, 2, 3 or 4, prepared by way of:

(i) providing hydroxycarboxylic acids of formula (V) or their ester-forming derivatives and, optionally, carboxylic acids or hydroxycarboxylic acids of formula (IV) or their ester-forming derivatives and alkylene glycol of formula (VI)

(ii) heating the mixture obtained in step (i) to at least 90° C. for a period of 0.1 milliseconds to 60 minutes, and (iii) cooling the product mixture obtained in step (ii) to 25° C. or below within a period of 1 second to 60 minutes.

2. The composition according to claim 1, characterized in that n is 2 or 3, and m is 1 or 2.

3. The composition according to claim 2, characterized in that n is 2, and m is 1.

4. The composition according to claim 1, characterized in that c and d are 1.

5. The composition according to claim 2, characterized in that c and d are 1.

6. The composition according to claim 1, characterized in that $R^2$ is a divalent residue with the formula —$C_0H_{20}$— or a trivalent residue with the formula —$C_pH_{2p-1}$< or a tetravalent residue with the formula >$C_qH_{2q-2}$<,
wherein o is an integer of 2 to 4, p is an integer of 1 to 4 and
q is an integer of 2 to 4.

7. The composition according to claim 1, wherein the composition is prepared by reacting malic acid, lactic acid, tartronic acid, tartaric acid, isocitric acid, citric acid, acetyl citric acid, or mucic acid with an alkylene glycol.

8. The composition according to claim 7, characterized in that $R^2$ and $R^3$ are residues of formula (Ib), (Ic), (Id), (Ie), (If) or (Ig)

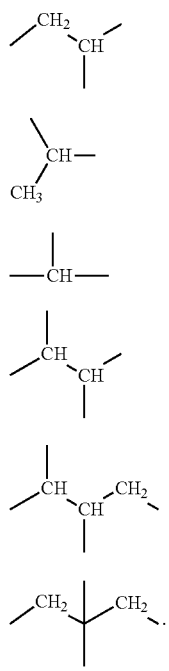

9. The composition according to claim 8, characterized in that $R^2$ and $R^3$ are residues derived from citric acid after the removal of the carboxyl groups and the hydroxyl group, each of $R^2$ and $R^3$ having the formula:

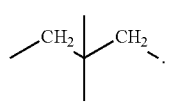

10. The composition according to claim 1, characterized in that a and b are 2, $R^2$ and $R^3$ are aliphatic hydrocarbon residues with three carbon atoms and that $R^1$ and $R^4$ are hydrogen, cations of alkali metals, cations of alkaline earth metals, quarternary ammonium cations or residues of formula —$(C_nH_{2n}$—$O)_m$—H.

11. The composition according to claim 1, characterized in that the composition has compounds of a structure of the formula (II) or their alkaline or alkaline earth salts or partial neutralisates thereof

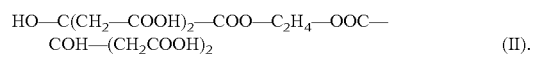     (II).

12. The composition according to claim 1, wherein the composition has a viscosity of from 100 to 2000 mPas at 20° C.

13. The composition according to claim 1, characterized in that the compounds of Formula (I) have a residue of the formula $(R^1OOC)_a$—$R^2(OH)COO$— and a residue of the formula $(R^4OOC)_b$—$R^3(OH)COO$—, wherein these residues have the same meaning.

14. The composition according to claim 1, characterized in that the heating in step ii) is carried out by irradiation of microwave radiation.

15. The composition according to claim 1, characterized in that the mixture in step ii) is heated to a temperature between 140 and 160° C. and that the time period of heating is between 1 and 120 seconds.

16. The composition according to claim 1, wherein the compounds of formula (I) are complexed with metal cations.

17. The composition according to claim 1, present in a washing and cleaning agent in an amount of from 0.5 to 6 wt. % based on the total weight of the cleaning agent.

18. The composition according to claim 1 incorporated into a cleaning agent for the cleaning of dishes comprising:
(i) 5 to 65 wt. % of a water-soluble builder component,
(ii) 5 to 20 wt. % of a peroxygen compound,
(iii) 0.5 to 25 wt. % of the composition according to claim 1, and
(iv) 0 to 50 wt. % of additional additives such as enzymes, alkali carriers, surface-active agents, pH regulators, organic solvents or other adjuvants, such as glass corrosion inhibitors, silver corrosion inhibitors and foam regulators, each based on the total weight of the cleaning agent.

* * * * *